United States Patent [19]

Umezawa et al.

[11] Patent Number: 4,547,567

[45] Date of Patent: Oct. 15, 1985

[54] DERIVATIVES OF 4'-DEMETHYL-4-EPIPODOPHYLLOTOXIN

[75] Inventors: Hamao Umezawa; Tomio Takeuchi, both of Tokyo; Shinichi Kondo, Yokohama; Wataru Tanaka, Houya; Tomohisa Takita, Asaka; Yoshio Nishimura, Yokohama; Hiroshi Yoshikawa, Fujioka, all of Japan

[73] Assignee: Zaidan Hojin Biseibutsu Kagaku Kenkyu Kai, Tokyo, Japan

[21] Appl. No.: 631,999

[22] Filed: Jul. 18, 1984

[30] Foreign Application Priority Data

Jul. 29, 1983 [JP] Japan ................... 58-137687

[51] Int. Cl.$^4$ ............................. C07H 15/24
[52] U.S. Cl. .......................... 536/17.2; 536/18.1
[58] Field of Search ..................... 536/17.2, 18.1

[56] References Cited

U.S. PATENT DOCUMENTS 3,060,169 10/1962 Stoll et al. ................. 536/18.1
3,408,441 10/1968 von Wartburg et al. ........... 536/18.1
3,524,844 8/1970 Keller-Juslem et al. .......... 536/18.1

*Primary Examiner*—Johnnie R. Brown
*Attorney, Agent, or Firm*—Banner, Birch, McKie & Beckett

[57] ABSTRACT

This invention relates to novel 4'-demethyl-4-epipodophyllotoxin derivatives represented by the general formula (I), and salts thereof:

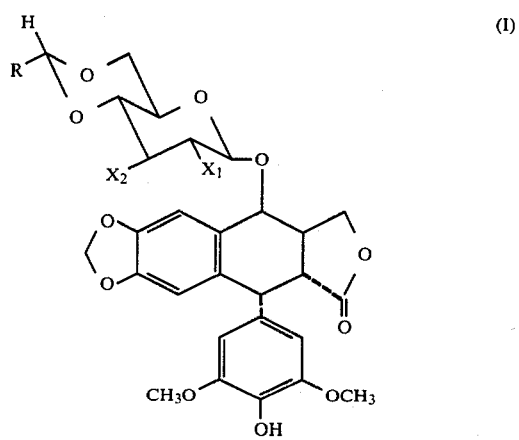

wherein R is a lower alkyl group, and $X_1$ and $X_2$ are independently a hydroxyl group or an amino group, the one being an amino group and the other being a hydroxyl group. These novel derivatives have a high carcinostatic activity and a relatively high water solubility and hence are expected to be useful as carcinostatics.

4 Claims, No Drawings

DERIVATIVES OF 4′-DEMETHYL-4-EPIPODOPHYLLOTOXIN

BACKGROUND OF THE INVENTION

4′-Demethyl-epipodophyllotoxin-alkylidene-β-D-glucoside (hereinafter referred to as "etoposide") has heretofore been well known as a compound having an antitumor effect by U.S. Pat. No. 3,524,844 and the like.

In order to develop a more excellent antitumor agent, the present inventors have made an extensive study and have consequently found that a compound of the general formula (I) has an excellent antitumor activity and has a very high water solubility as compared with etoposide, whereby this invention has been accomplished.

SUMMARY OF THE INVENTION

An object of this invention is to provide novel 4′-demethyl-4-epipodophyllotoxin derivatives having an excellent antitumor activity and a high water solubility, salts thereof and a process for producing them.

Other objects and advantages of this invention will be made apparent by the following descriptions.

DETAILED DESCRIPTION OF THE INVENTION

This invention relates to novel 4′-demethyl-4-epipodophyllotoxin derivatives represented by the general formula (I), and salts thereof:

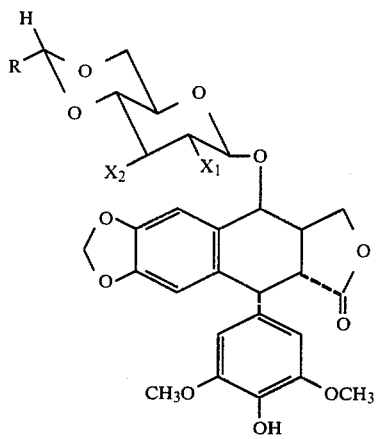

wherein R is a lower alkyl group, and $X_1$ and $X_2$ are independently a hydroxyl group or an amino group, the one being an amino group and the other being a hydroxyl group.

The compound of the above general formula (I) of this invention can be obtained by reacting a compound represented by the general formula (V):

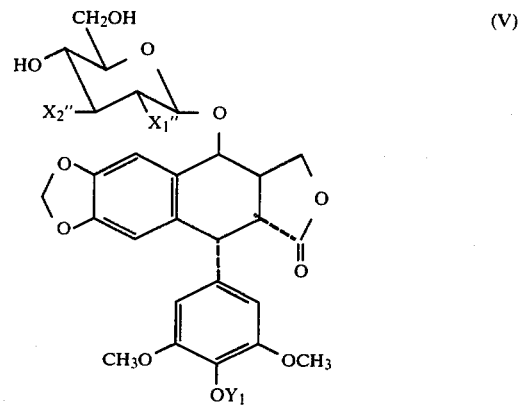

wherein one of $X_1''$ and $X_2''$ is a hydroxyl group or a protected hydroxyl group and the other is an amino group or a protected amino group, and $Y_1$ is hydrogen or a protecting group, with an aldehyde represented by the general formula (VI), or an acetal compound thereof:

wherein R is a lower alkyl group, to obtain a compound represented by the general formula (VII):

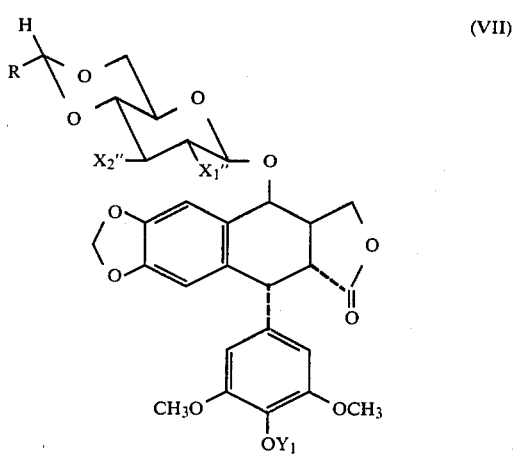

wherein $X_1''$, $X_2''$ and $Y_1$ are as defined above, and then removing protecting groups by a conventional method to obtain the general formula (I) when the general formula (VII) contains the protecting group, but when $X_1''$, $X_2''$ and $Y_1$ in the general formula (VII) do not contain the protecting group, the general formula (VII) becomes the same as the general formula (I).

The reaction of a compound of the general formula (V) with an aldehyde of the general formula (VI) or an acetal compound thereof is usually effected in a solvent in the presence of an acid catalyst, preferably, a sulfonic acid, cation-exchange resin and Lewis acid. The molar ratio of (VI) to (V) is usually 0.5 to 100, preferably 1 to 10. As the sulfonic acid, arylsulfonic acids such as p-toluenesulfonic acid and the like are preferred, and the used amount thereof is usually 0.01 to 10% by weight preferably 0.1 to 5% by weight based on the sum of the compounds of (V) and (VI).

The solvent is not limited so long as it is inert, and there may usually be used, for example, polar organic solvents such as acetonitrile, nitromethane, dioxane and the like.

The reaction temperature is usually at −10° C. to 100° C., preferably −5° C. to 50° C., more preferably 0° C. to 30° C. The reaction time is 5 minutes to 10 hours, preferably 10 minutes to 3 hour.

For the removal of the protecting groups from the compound of the general formula (VII), there may be employed any of the well-known methods and the methods include reduction (e.g., catalytic reduction using a Pd catalyst or a Pt catalyst), acid decomposition (e.g., acid decomposition using hydrogen halogenide such as HCl and HBr, acetic acid, trifluoroacetic acid, trifluoromethanesulfonic acid or the like), a method of removing the protecting groups by reacting an amine with said compound, a method of removing the protecting groups by reacting an alcohol (a lower alcohol such as methanol, ethanol or the like) with said compound in the presence of a catalyst (e.g., zinc powder, lead powder or a metal salt of an organic acid such as zinc acetate or the like), etc.

The lower alkyl group for R in the general formula (VI) includes, for example, a methyl group, an ethyl group, a propyl group, etc., and a methyl group is particularly preferred.

The aldehyde of the general formula (VI) or the acetal thereof include, for example, acetaldehyde, propionaldehyde, and acetaldehyde diloweralkylacetal such as acetaldehyde dimethylacetal, acetaldehyde diethylacetal and acetaldehyde dipropylacetal.

The kinds of protecting group for the amino group and the protecting group for the hydroxyl group in the general formula (V) or (VII) are not critical.

For example, the protecting group for the amino group includes lower alkoxycarbonyl groups such as butoxycarbonyl group, benzyloxycarbonyl group and substituted benzyloxycarbonyl groups having on the phenyl group one or more substituents (for example, lower alkyl groups, lower alkoxy groups, halogen atoms such as Cl or Br, or the like), a benzyl group, halogen-substituted lower acyl groups (e.g., a trifluoroacetyl group, a monochloroacetyl group, etc.), and the like.

The protecting group for the hydroxyl group includes lower acyl groups such as an acetyl group, halogen-substitued acetyl groups and the like, a pyranyl group, the aryl-substituted lower-alkoxycarbonyl groups exemplified above as the aforesaid protecting group for the amino group, etc.

The compound of the general formula (V) is produced in the following process.

4′-O-protected-4′-demethyl-4-epipodophyllotoxin represented by the general formula (II):

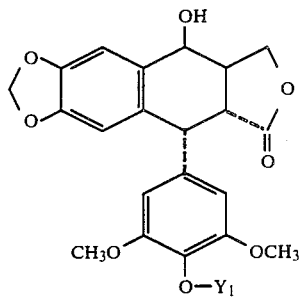

wherein $Y_1$ is as defined above, is reacted with a compound represented by the general formula (III):

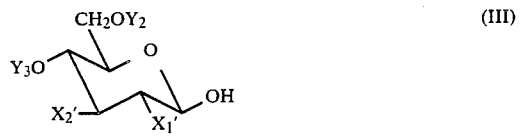

wherein $Y_2$ and $Y_3$ are independently a protecting group, one of $X_1'$ and $X_2'$ is a protected amino group and the other is a protected hydroxyl group, in an inert solvent in the presence of a catalyst for condensation, for example, boron trifluoride-diethyl ether or the like to obtain a compound represented by the general formula (IV):

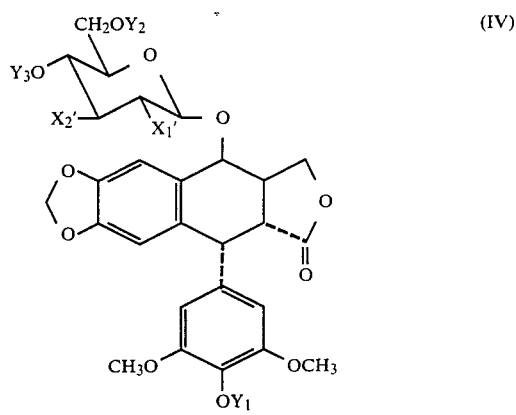

wherein $Y_1$, $Y_2$, $Y_3$, $X_1'$ and $X_2'$ are as defined above. Subsequently, the protecting groups for $Y_2$ and $Y_3$ are removed. At the time of removing the protecting groups for $Y_2$ and $Y_3$, the protecting group for the hydroxyl group in $X_1'$ or $X_2'$ and $Y_1$ may be removed, and if necessary, the remaining protecting group or groups in $X_1'$ and/or $X_2'$ and the protecting group for $Y_1$ may be then removed if $Y_1$ is a protecting group.

Thus, the compound of the general formula (V) can be obtained.

The compound of the general formula (I) of this invention can be converted into a salt thereof with an acid by a conventional method, and as the salt, there may be exemplified salts with inorganic acids or organic acids such as hydrochloric acid, sulfuric acid, phosphoric acid, acetic acid, citric acid or the like.

Next, typical compounds of this invention and their physical property values are shown below.

(1)    4-O-(2-amino-2-deoxy-4,6-O-ethylidene-β-D-glucopyranosyl)-4′-demethyl-4-epipodophyllotoxin. (Compound No. 1) (hereinafter referred to as 2-amino compound)

Melting point: 201°–215° C.
Specific rotation: $[\alpha]_D^{21} -89.8°$ (CH$_3$OH)
MS (SIMS): 588 (M+H)$^+$
NMR (Pyridine-d$_5$): δ1.36 (3H, d, CH$_3$), δ3.74 (6H, s, OCH$_3$), δ5.05 (1H, d, H-4), δ5.24 (1H, d, H-1), δ5.92 (2H, s, —O—CH$_2$—O—), δ6.72 (1H, s, H-8), δ6.75 (2H, s, H-2′, 6′), δ7.45 (1H, s, H-5)
IR: 1764 (C=O)cm$^{-1}$ (2)    4-O-(3-amino-3-deoxy-4,6-O-ethylidene-β-D-glucopyranosyl)-4′-demethyl-4-epipodophyllotoxin. (Compound No. 2) (hereinafter referred to as 3-amino compound)

Melting point: 210°–220° C.
Specific rotation: $[\alpha]_D^{23} -94.7°$ (CHCl$_3$)
MS (SIMS): 588 (M+H)+
NMR (CDCl$_3$): $\delta 1.35$ (3H, d, CH$_3$), $\delta 3.77$ (6H, s, —OCH$_3$), $\delta 4.90$ (1H, d, H—4), $\delta 5.97$ (2H, broad s, —O—CH$_2$—O—), $\delta 6.27$ (2H, s, H-2', 6'), $\delta 6.55$ (1H, s, H-8), $\delta 6.85$ (1H, s, H-5)
IR: 1765 (C=O)cm$^{-1}$ These compounds have very potent antitumor activity.

The antitumor activity of the compound according to this invention was investigated in the following way:

EXPERIMENTAL EXAMPLE 1

(Test of Antitumor Activity)

$10^5$ murine leukemia L1210 cells were inoculated intraperitoneally into mice, and a suspension of the compound of this invention in physiological saline solution was administered intraperitoneally once daily for 9 consecutive days, starting 24 hours after the inoculation. The animals were observed for 41 days, and the survival rates (T/C) in these animals were calculated from the following equation:

$$T/C(\%) = \frac{\text{Average period (in days) of survival in the group receiving the compound of this invention}}{\text{Average period (in days) of survival in the control group}} \times 100$$

The control group was administered physiological saline solution only. The average survival period for the control group was 7.9 to 8.3 days.

Compound No. 1 in a dose of 100 μg/mouse/day was found to give T/C of 494 or more, and Compound No. 2 in a dose of 25 μg/mouse/day, T/C of 430 or more.

EXPERIMENTAL EXAMPLE 2

(Test of Antitumor Activity)

$10^5$ murine leukemia L1210 cells were inoculated into mice (female CDF$_1$, 6 weeks old), and the hydrogen chloride salt of Compound No. 1 (2-amino compound) was administered intraperitoneally once daily for 5 consecutive days, starting 24 hours after the inoculation. The control group was administered physiological saline solution alone in the same manner as described above. Whether the animals were alive or dead was observed for 60 days after the beginning of the administration and the survival rates were calculated in the same manner as in Experimental Example 1 to find that when Compound No. 1 was administered in a dose of 10 mg/kg, the survival rates (T/C %) was 597 and the average survival period was 43.6±23.5 days. On the 60th day, mice which survived were three of six mice per group.

As is evident from these results, the compounds of this invention have a very excellent antitumor effect.

EXPERIMENTAL EXAMPLE 3

(Solubility test)

In a test tube was placed 11.75 mg of the hydrogen chloride salt of Compound No. 1 (2-amino compound), and 0.5 ml of distilled water was added. The test tube was stored at 25° C. with occasional shaking, and after 6 hr and 29 hr, sampling in an amount of 50 μl each was conducted. After each sample was filtered, 30 μl of the filtrate was diluted with 4 ml of water, and then the absorbance at 285 nm was measured.

The concentration was calculated assuming that $E_1^{cm 1\%}$ (285 nm, H$_2$O)=59.6. The results are shown below.

|  | OD$_{285}$ | Concentration |
|---|---|---|
| 6 hr | 62.03 | 10.4 mg/ml |
| 29 hr | 64.08 | 10.7 mg/ml |

Etoposide was examined for water solubility by the same test as described above to find that its concentration was 0.1 mg/ml.

Compound No. 2 (the hydrogen chloride salt of the 3-amino compound) was examined for water solubility in the same manner as described above to show substantially the same water solubility as that of Compound No. 1 (the hydrogen chloride salt of the 2-amino compound).

The results described above indicate that the compounds of this invention are very superior to etoposide in water solubility.

The synthesis of the compounds according to this invention will be described in greater detail with reference to the following Examples:

EXAMPLE 1

(1) Synthesis of 4-O-(2-benzyloxycarbonylamino-2-deoxy-β-D-glucopyranosyl)-4'-benzyloxycarbonyl-4'-demethyl-4-epipodophyllotoxin (a) 500 mg of 4'-benzyloxycarbonyl-4'-demethyl-4-epipodophyllotoxin and 620 mg of 3,4,6-tri-O-acetyl-2-benzyloxycarbonylamino-2-deoxy-β-D-glucopyranose were dissolved in 1 ml of dichloromethane. In the solution cooled at −18° C., 0.5 ml of BF$_3$.Et$_2$O was added dropwise over 3 minutes, and the mixture was reacted for 30 minutes, in an atmosphere of argon. 0.5 ml of pyridine was added to terminate the reaction, and the reaction mixture was diluted with 20 ml of dichloromethane. The organic layer was washed twice with 10 ml of water, dried over anhydrous Na$_2$SO$_4$, and concentrated. The concentrate was subjected to silica gel chromatography for separation and purification. 700 mg of 4-O-(3,4,6-tri-O-acetyl-2-benzyloxycarbonylamino-2-deoxy-β-D-gluropyranosyl)-4'-benzyloxycarbonyl-4'-demethyl-4-epipodophyllotoxin was obtained.

Specific rotation: $[\alpha]_D^{21} -39.6°$ (CHCl$_3$)

(b) 600 mg of the compound obtained in the above step and 115 mg of zinc acetate were dissolved in 5 ml of methanol, and the solution was boiled for 6 hours under reflux to cause the reaction. The reaction mixture was evaporated to dryness, and 20 ml of dichloromethane and 10 ml of water were added to the residue. The mixture was shaken vigorously, and the organic layer was separated. The separated layer was dried over anhydrous Na$_2$SO$_4$ and concentrated. The concentrate was subjected to silica gel chromatography for separation and purification. 295 mg of 4-O-(2-benzyloxycarbonylamino-2-deoxy-β-D-glucopyranosyl)-4'-benzyloxycarbonyl-4'-demethyl-4-epipodophyllotoxin was obtained.

Specific rotation: $[\alpha]_D^{17} -57.2°$ (CHCl$_3$)

(2-1) Synthesis of
4-O-(2-amino-2-deoxy-4,6-O-ethylidene-β-D-glucopyranosyl)-4'-demethyl-4-epipodophyllotoxin (a) 60 mg of 4-O-(2-benzyloxycarbonylamino-2-deoxy-β-D-glucopyranosyl)-4'-benzyloxycarbonyl-4'-demethyl-4-epidodophyllotoxin in the above step was dissolved in a solvent mixture of 1 ml of water and 2 ml of acetone. 10 mg of palladium black was added to the solution, and the mixture was stirred for 3 hours, with hydrogen blown therethrough, to perform reduction. The reaction mixture was filtered, and the filtrate was concentrated to dryness. The concentrate was subjected to silica gel chromatography for separation and purification. 70 mg of 4-O-(2-amino-2-deoxy-β-D-glucopyranosyl)-4'-demethyl-4-epipodophyllotoxin was obtained.

Specific rotation: $[\alpha]_D^{17} - 74.7$ (CH$_3$OH)

(b) 50 mg of the compound obtained in the above step and 0.5 ml of acetaldehyde diethylacetal were dissolved in 2 ml of acetonitrile. 2 mg of p-toluenesulfonic acid was added to the solution, and the mixture was stirred for 30 minutes at room temperature. Sodium bicarbonate was added to the mixture, and the insolubles were separated by filtration. The filter cake was washed with dichloromethane, and the washings were combined with the filtrate, followed by concentrating the combined liquid. The concentrate was chromatographed on cilica gel for separation and purification. 45 mg of 4-O-(2-amino-2-deoxy-4,6-O-ethylidene-β-D-glucopyranosyl)-4'-demethyl-4-epipodophyllotoxin was obtained.

In this process, cation-exchange resin such as Amberlite®200 or Lewis acid such as ZnCl$_2$ in place of p-toluenesulfonic acid could be used as catalyst for condensation.

(2-2) Synthesis of
4-O-(2-amino-2-deoxy-4,6-O-ethylidene-β-D-glucopyranosyl)-4'-demethyl-4-epipodophyllotoxin (a) 180 mg of 4-O-(2-benzyloxycarbonylamino-2-deoxy-β-D-glucopyranosyl)-4'-benzyloxycarbonyl-4'-demethyl-4-epipodophyllotoxin and 0.5 ml of acetaldehyde diethylacetal were dissolved in 5 ml of acetonitrile. 10 mg of p-toluenesulfonic acid was added to the solution, and the mixture was stirred for 30 minutes at room temperature. Sodium bicarbonate was added to the mixture, and the insolubles were separated by filtration. The filter cake was washed with dichloromethane, and the washings were combined with the filtrate, followed by concentrating the combined liquid. The concentrate was chromatographed on silica gel for separation and purification. 171 mg of 4-O-(2-benzyloxycarbonylamino-2-deoxy-4,6-O-ethylidene-β-D-glucopyranosyl)-4'-benzyloxycarbonyl-4'-demethyl-4-epipodophyllotoxin was obtained.

Specific rotation: $[\alpha]_D^{18} - 54.1°$ (CHCl$_3$)

In this process, acetaldehyde in place of acetaldehyde diethylacetal was used and treated as the same way to obtain the object compound.

(b) 171 mg of the compound obtained in the above step was dissolved in a solvent mixture of 3 ml of ethyl acetate and 2 ml of acetone. 10 mg of palladium black was added to the solution, and the mixture was stirred for 3 hours, with hydrogen blown therethrough, to perform reduction. The reaction mixture was filtered, and the filtrate was concentrated to dryness. Recrystallization from ethyl acetate gave 73 mg of the desired 4-O-(2-amino-2-deoxy-4,6-O-ethylidene-β-D-glucopyranosyl)-4'-demethyl-4-epipodophyllotoxin. The mother liquor was chromatographed on silica gel for separation and purification. The desired compound was recovered in an amount of 15 mg.

EXAMPLE 2

Synthesis of
4-O-(3-amino-3-deoxy-4,6-O-ethylidene-β-D-glucopyranosyl)-4'-demethyl-4-epipodophyllotoxin (1) Synthesis of
4-O-(2-O-acetyl-3-benzyloxycarbonylamino-2-deoxy-β-D-glucopyranosyl)-4'-benzyloxycarbonyl-4'-demethyl-4-epipodophyllotoxin (a) 486 mg of 4'-benzyloxycarbonyl-4'-demethyl-4-epipodophyllotoxin and 360 mg of 2,4,6-tri-O-acetyl-3-benzyloxycarbonylamino-3-deoxy-β-D-glucopyranose were dissolved in 1 ml of dichloromethane. In the solution cooled at −20° C., 0.5 ml of Bf$_3$.Et$_2$O was added dropwise over 3 minutes, and the mixture was reacted for 30 minutes, with stirring, in an atmosphere of argon. 0.5 ml of pyridine was added to terminate the reaction, and then, the reaction mixture was diluted with 20 ml of dichloromethane. The dilution was washed twice with 10 ml of water, and the organic layer was dried over anhydrous Na$_2$SO$_4$ and concentrated. The concentrate was separated and purified by silica gel chromatography to obtain 500 mg of 4-O-(2,4,6-tri-O-acetyl-3-benzyloxycarbonylamino-3-deoxy-β-D-glucopyranosyl)-4'-benzyloxycarbonyl-4'-demethyl-4-epipodophyllotoxin.

Specific rotation: $[\alpha]_D^{19} - 40.1°$ (CHCl$_3$)

(b) 500 mg of the compound obtained in the above step and 100 mg of zinc acetate were dissolved, with heating, in a solvent mixture of 2 ml of methanol and 2 ml of dioxane. The solution was boiled for 6 hours under reflux, and the reaction mixture was concentrated to dryness. 20 ml of dichloromethane and 10 ml of water were added to the residue, and the mixture was shaken vigorously. The organic layer was separated from the system, dried over anhydrous Na$_2$SO$_4$, and concentrated. The concentrate was separated and purified by silica gel chromatography to obtain 155 mg of 4-O-(2-O-acetyl-3-benzyloxycarbonylamino-3-deoxy-β-D-glucopyranosyl)-4'-benzyloxycarbonyl-4'-demethyl-4-epipodophyllotoxin.

Specific rotation: $[\alpha]_D^{18} - 31.8°$ (CHCl$_3$)

(2) Synthesis of
4-O-(3-amino-3-deoxy-4,6-O-ethylidene-β-D-glucopyranosyl)-4'-demethyl-4-epipodophyllotoxin (2-1) (a) 140 mg of the compound obtained in Step (b) and 0.5 ml of acetaldehyde diethylacetal were dissolved in 3 ml of acetonitrile. 5 mg of p-toluenesulfonic acid was added to the solution, and the mixture was reacted for 2 hours at room temperature with stirring. Sodium bicarbonate was added, and the insolubles were collected by filtration. The filter cake was washed with dichloromethane, and the washings were combined with the filtrate, followed by concentrating the combined liquid. The concentrate was separated and purified by chromatography to obtain 106 mg of 4-O-(2-acetyl-3-benzyloxycarbonylamino-3-deoxy-4,6-O-ethylidene-β-D-glucopyranosyl)-4'-benzyloxycarbonyl-4-demethyl-4-epipodophyllotoxin.

Specific rotation: $[\alpha]_D^{25} - 35.8°$ (CHCl$_3$)

(b) 100 mg of the compound obtained in Step (a) was dissolved in 3 ml of ethyl acetate, and palladium black was added to the solution. The mixture was stirred for 3 hours in a hydrogen gas stream for reduction. The reaction mixture was filtered and concentrated. The concentrate was separated and purified by silica gel chromatography to obtain 39 mg of 4-O-(2-O-acetyl-3-amino-3-deoxy-4,6-O-ethylidene-β-D-glucopyranosyl)-4'-demethyl-4-epipodophyllotoxin.

NMR (CDCl$_3$) δ1.35 (3H, d, CH$_3$),

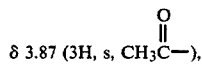

δ 3.87 (3H, s, CH$_3$C—),

δ3.88 (6H, s, —OCH$_3$), δ4.81 (1H, d, H-4), δ5.97 (2H, s, —OCH$_2$O—), δ6.24 (2H, s, H-2', 6'), δ6.53 (1H, s, H-8), δ6.85 (1H, s, H-5)

(c) 29 mg of the compound obtained in Step (b) and 5 mg of zinc acetate were dissolved in 3 ml of methanol, and the solution was boiled for 45 minutes under reflux. The reaction mixture was poured into 10 ml of water, and then extracted twice with 10 ml of dichloromethane. The extract was concentrated, and the concentrate was separated and purified by silica gel chromatography to obtain 7.4 mg of 4-O-(3-amino-3-deoxy-4,6-O-ethylidene-β-D-glucopyranosyl)-4'-demethyl-4-epipodophyllotoxin.

REFERENTIAL EXAMPLE

Synthesis of a Saccharide 700 mg of 3,4,6-tri-O-acetyl-2-benzyloxycarbonylamino-2-deoxy-α-D-glucopyranosyl bromide [Bull, Chem. Soc. Japn., 34, 183 (1963)] was dissolved in 2 ml of acetone, and with the solution cooled to 0° C, 290 mg of silver carbonate and 20 ml of water were added. The mixture was stirred for 1 hour at this temperature and filtered. The filtrate was concentrated to obtain 580 mg of 3,4,6-tri-O-acetyl-2-benzyloxycarbonylamino-2-deoxy-β-D-glucopyranose.

In this Referential Example, if 2,4,6-tri-O-acetyl-3-benzyloxycarbonylamino-3-deoxy-αD-glucopyranosyl bromide was used as the starting compound and treated in the same way, 2,4,6-tri-O-acetyl-3-benzyloxycarbonylamino-3-deoxy-β-D-glucopyranose could be obtained.

What is claimed is:

1. A novel 4'-demethyl-4-epipodophyllotoxin derivative represented by the formula, or a salt thereof:

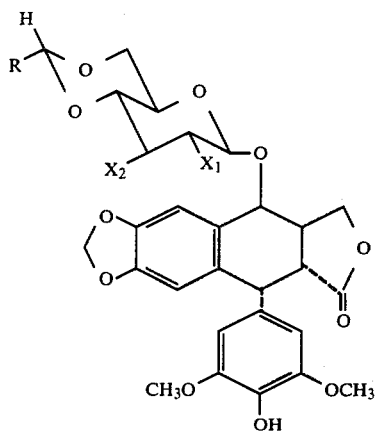

wherein R is a lower alkyl group, and X$_1$ and X$_2$ are independently a hydroxyl group or an amino group, when one is an amino group the other is a hydroxyl group.

2. A 4'-demethyl-4-epipodophyllotoxin derivative or a salt thereof according to claim 1, wherein R is a methyl group, an ethyl group or a propyl group.

3. 4-O-(2-amino-2-deoxy-4,6-O-ethylidene-β-D-glucopyranosyl)-4'-demethyl-4-epipodophyllotoxin and salts thereof.

4. 4-O-(3-amino-3-deoxy-4,6-O-ethylidene-β-D-glucopyranosyl)-4'-demethyl-4-epipodophylotoxin and salts thereof.

* * * * *